United States Patent [19]

Drust et al.

[11] Patent Number: 5,026,556
[45] Date of Patent: Jun. 25, 1991

[54] COMPOSITIONS FOR THE TRANSDERMAL DELIVERY OF PHARMACEUTICAL ACTIVES

[75] Inventors: Eugene G. Drust, Norwich, N.Y.; Gerald B. Kasting, Wyoming, Ohio; Ronald L. Smith; Joan B. Szkutak, both of West Chester, Ohio

[73] Assignee: Norwich Eaton Pharmaceuticals, Inc., Norwich, N.Y.

[21] Appl. No.: 269,944

[22] Filed: Nov. 10, 1988

[51] Int. Cl.$^5$ .................. A61F 13/00; A61L 15/03; A61K 9/06
[52] U.S. Cl. ............................ 424/449; 424/448; 514/289; 514/947
[58] Field of Search .............. 424/448, 449; 514/282, 514/947

[56] References Cited

U.S. PATENT DOCUMENTS

| | | | |
|---|---|---|---|
| 3,053,255 | 9/1962 | Meyer | 128/268 |
| 3,433,791 | 3/1969 | Bentley | 260/285 |
| 3,598,123 | 8/1971 | Zaffaroni | 128/268 |
| 4,031,894 | 6/1977 | Urquhart et al. | 128/268 |
| 4,060,084 | 11/1977 | Chandrasekaran et al. | 128/260 |
| 4,201,211 | 5/1980 | Chandrasekaran et al. | 128/268 |
| 4,299,826 | 11/1981 | Luedders | 424/181 |
| 4,379,454 | 4/1983 | Campbell et al. | 604/897 |
| 4,537,776 | 8/1985 | Cooper | 514/424 |
| 4,537,776 | 8/1985 | Cooper | 514/424 |
| 4,540,564 | 9/1985 | Bodor | 424/176 |
| 4,552,872 | 11/1985 | Cooper et al. | 514/175 |
| 4,557,934 | 12/1985 | Cooper | 424/128 |
| 4,573,995 | 3/1986 | Chen et al. | 514/282 |
| 4,590,190 | 5/1986 | Saito | 514/221 |
| 4,593,048 | 6/1986 | Sato et al. | 514/778 |
| 4,626,539 | 12/1986 | Aungst et al. | 514/282 |
| 4,806,341 | 2/1989 | Chien et al. | 424/449 |
| 4,806,341 | 2/1989 | Chien | 424/448 |
| 4,824,850 | 4/1989 | Bodor | 514/770 |
| 4,829,070 | 5/1989 | Bodor | 514/307 |
| 4,844,903 | 7/1989 | Seth | 424/449 |
| 4,879,297 | 11/1989 | Mahjour et al. | 514/232 |

FOREIGN PATENT DOCUMENTS

| | | | |
|---|---|---|---|
| 0043738 | 1/1982 | European Pat. Off. | |
| 0171742 | 2/1986 | European Pat. Off. | 514/282 |
| 0282156 | 9/1988 | European Pat. Off. | 514/282 |
| 3634016 | 10/1987 | Fed. Rep. of Germany | 514/282 |

Primary Examiner—Shep K. Rose
Attorney, Agent, or Firm—David L. Suter; Karen F. Clark; Jack D. Schaeffer

[57] ABSTRACT

Compositions for the transdermal delivery of buprenorphine comprising a safe and effective amount of buprenorphine in a carrier comprising:

(a) a polar solvent material selected from the group consisting of $C_3$–$C_4$ diols, $C_3$–$C_6$ triols, and mixtures thereof; and (b) a polar lipid material selected from the group consisting of fatty alcohol esters, fatty acid esters, and mixtures thereof;

wherein said polar solvent material and said polar lipid material are present in a weight ratio of solvent material:lipid material of from about 60:40 to about 99:1. Preferably, the polar solvent material is propylene glycol, and the polar lipid material is an ester of a $C_8$–$C_{12}$ fatty alcohol or fatty acid. Particularly preferred polar lipid materials include methyl laurate and methyl caprylate. The ratio of polar solvent material to polar lipid material is preferably from about 90:10 to about 98:2.

18 Claims, No Drawings

COMPOSITIONS FOR THE TRANSDERMAL DELIVERY OF PHARMACEUTICAL ACTIVES

BACKGROUND OF THE INVENTION

This invention relates to novel compositions for delivery of pharmaceutical active materials through the skin of humans and other animals. In particular, this invention relates to compositions for systemic administration of lipophilic drugs, such as buprenorphine, by topical application.

The pharmaceutical literature describes many methods for systemic delivery of pharmaceutical active materials, i.e., delivery of actives to internal organs via the circulatory system. Typically, such methods are either parenteral (by intravenous or intramuscular injection) or enteral (by oral ingestion). However, methods are also described for delivery of active materials transdermally, i.e., systemic delivery through the skin from a topically applied composition. Such compositions may be applied to the skin as an ointment, for example. Alternatively, many devices are known in the literature which contain a set quantity of the composition in close proximity to the skin allowing the active to contact and penetrate the skin. These devices are commonly referred to as "transdermal patches".

Transdermal administration of pharmaceutical actives may offer many advantages, at least in theory. Transdermal delivery is often more convenient than parenteral or enteral administration, avoiding the need for injections or repeated administration of oral dosages. Therefore, compliance with therapeutic regimens, which is often critical, can be improved. Precise control of the dosage may also be afforded, avoiding potential overdoses. Blood levels of the active may be more stable and uniform (without sharp "peaks"), thereby reducing side effects. Further, transdermal delivery may avoid complications associated with enteral administration of pharmaceutical actives. For example, variable rates of absorption through the gastrointestinal tract, gastrointestinal irritation, and hepatic first-pass metabolism may be avoided.

In reality, however, transdermal administration is difficult or even impossible for certain pharmaceutical actives. The skin is highly impermeable, because it must serve as a barrier to pathogens and toxic materials, while also containing the fluids of the body. Much of this impermeability results from the layers of skin created by normal development and physiological changes.

After cells are formed in the basal layer of the skin, they begin to migrate toward the surface until they are eventually sloughed off. As they undergo this migration, they progressively become more dehydrated and keratinized. When they reach the surface, just prior to being sloughed off, they form a thin layer of dense, metabolically inactive cells approximately 10 microns thick. This layer is called the stratum corneum. As a result of the high degree of keratinization, the cells of the stratum corneum provide a formidable barrier.

Thus, in order to achieve systemic delivery, transdermal administration involves penetration of an active material through the dense, lipophilic layer of keratinized skin, as well as through the hydrated basal layers of the skin, in order to reach the circulatory system. Not surprisingly, the ability to achieve this transdermal delivery may depend upon many factors, including (for example) the molecular size of the pharmaceutical active material, its hydrophilic/lipophilic characteristics, and the presence of other materials applied to the skin along with the active material.

The literature is replete with many formulations designed to achieve transdermal delivery of various active materials. Typically, these formulations optimize delivery of a single material, or a small class of materials. See, for example, R. W. Baker et al., *Pharmaceutical Technology* 1987 26 (1987). Topical compositions containing a lower alkyl diol and a cell envelope disordering compound, for delivery of a variety of lipophilic active materials, are described in European Patent Publication No. 43,738, Wickett et al., published Jan. 13, 1982. Similar compositions for the delivery of corticosteroids are described in U.S. Pat. No. 4,552,872, Cooper et al., issued Nov. 12, 1985. Compositions for the transdermal delivery of naloxone, naltrexone and nalbuphine, using polyethylene glycol monolaurate, are described in U.S. Pat. No. 4,573,995, Chen et al., issued Mar. 4, 1986. Compositions for the delivery of actives using higher monoalcohols and various solvents such as thio glycerols and lactic acid esters, are described in U.S. Pat. No. 4,590,190, Saito et al., issued May 20, 1986. Compositions containing a lower alcohol and an adjuvant such as an aliphatic hydrocarbon, or a monohydric alcohol ester of an aliphatic carboxylic acid, are described in U.S. Pat. No. 4,593,048, Sato et al., issued June 3, 1986. Pharmaceutical compositions for the transdermal delivery of opioids, using propylene glycol with fatty alcohols or fatty acids, are described in U.S. Pat. No. 4,626,539, Aungst et al., issued Dec. 2, 1986.

While many such delivery systems are known, they may not be acceptable for delivery of certain active materials, for a variety of reasons. For example, the formulations must provide for sufficient flux of the active material through the skin so as to obtain and maintain adequate systemic delivery. This is particulary important since the available skin surface for application is typically confined, for practical reasons, to less than about 100 cm$^2$ (15.5 in$^2$). Compositions must also provide for delivery of the active material while minimizing side effects such as (for example) skin irritation. Further, compositions must be stable, allowing use after extended periods of storage. They should also be compatible with excipient materials, such as gelling agents, in order to allow tailoring of dosage forms to specific needs.

SUMMARY OF THE INVENTION

The present invention provides compositions for the transdermal delivery of buprenorphine comprising a safe and effective amount of buprenorphine in a carrier comprising:

(a) a polar solvent material selected from the group consisting of $C_3$-$C_4$ diols, $C_3$-$C_6$ triols, and mixtures thereof; and (b) a polar lipid material selected from the group consisting of fatty alcohol esters, fatty acid esters, and mixtures thereof;

wherein said polar solvent material and said polar lipid material are present in a weight ratio of solvent material:lipid material of from about 60:40 to about 99:1.

Preferably, the polar solvent material is propylene glycol, and the polar lipid material is an ester of a $C_8$-$C_{12}$ fatty alcohol or fatty acid. The ratio of polar solvent material to polar lipid material is preferably from about 90:10 to about 98:2.

It has now been discovered that certain lipophilic drugs, such as buprenorphine, may be systemically administered at effective levels by such compositions containing a lower alkyl diol and an ester of a fatty alcohol or fatty acid. In particular, such compositions provide efficacious administration of buprenorphine, for extended periods of time, without undue side effects (i.e., for example, having reduced skin irritation). These compositions are stable, aesthetically acceptable, and may be adapted to a variety of dosage forms, including transdermal patches.

DESCRIPTION OF THE INVENTION

The compositions of the present invention comprise a lipophilic pharmaceutical active material (such as buprenorphine) in a carrier of a polar solvent material and a polar lipid material, for administration to a human or other animal subject. Specific materials used in this invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition (including age) of the patient, the duration of treatment, the nature of concurrent therapy (if any), and the specific formulations employed.

Specifically, the compositions of this invention comprise a safe and effective amount of buprenorphine in a carrier comprising:

(a) a polar solvent material selected from the group consisting of $C_3$–$C_4$ diols, $C_3$–$C_6$ triols, and mixtures thereof; and (b) a polar lipid material selected from the group consisting of fatty alcohol esters, fatty acid esters, and mixtures thereof;

wherein said polar solvent material and said polar lipid material are present in a weight ratio of solvent material:lipid material of from about 60:40 to about 99:1.

The polar solvent material and polar lipid material are preferably present at a combined level (level of polar solvent plus polar lipid) of from about 70% to about 99.5%, more preferably from about 80% to about 99.5%, more preferably from about 90% to about 99.5%. (As used herein, all percentages are by weight of total composition.)

The weight ratio of polar solvent material to polar lipid material (polar solvent:polar lipid) is preferably from about 80:20 to about 99:1, more preferably from about 90:10 to about 98:2. These preferred ranges are, however, predicated on maximizing systemic delivery of buprenorphine through the skin. Other ratios of polar solvent:polar lipid may be desired in certain formulations, (for example) to enhance aesthetic characteristics, further reduce skin irritation, or to further increase stability of the formulations.

The useful ranges of polar solvent:polar lipid may subsume two phase systems, depending upon the solubility of the particular lipid material in the particular solvent material. Preferably, however, the compositions of this invention are single phase systems, i.e., wherein the polar lipid material is fully soluble in the polar solvent material, in the final formulation (including the active and all optional materials). Accordingly, for example, in compositions employing propylene glycol as the polar solvent material and methyl laurate as the polar lipid material, the ratio of polar solvent:polar lipid is preferably about 97:3. For compositions employing propylene glycol with methyl caprylate as a polar lipid material, the ratio is preferably from about 90:10 to about 95:5.

The safe and effective amount of buprenorphine in the compositions of this invention will depend, of course, on the condition to be treated, the desired flux characteristics of the specific composition used, and the desired duration of buprenorphine delivery from the composition. (As referred to herein, "flux" is the rate at which buprenorphine is transferred from the skin surface to the bloodstream). The compositions of this invention may include from about 1.0 mg (milligrams) to about 40 mg, preferably from about 2.0 mg to about 20 mg, more preferably from about 3.0 mg to about 10 mg of buprenorphine.

The specific amount of buprenorphine used in the compositions of this invention may also vary depending upon the solubility of buprenorphine in the other components of the composition (unless a suspension of buprenorphine is desired). The maximum amount of buprenorphine that may be soluble in the other components of the composition (the saturation level) will vary with the specific polar solvent material, polar lipid material, and optional materials present (such as solubilizers). This level may be determined by routine experimentation. Preferably, buprenorphine is present at a level of at least about 50% of saturation. More preferably, buprenorphine is present at a level of at least about 80%, more preferably at least about 90% of saturation.

The compositions of this invention are preferably provided in unit dosage form. As used herein, a "unit dosage form" is a composition of this invention containing an amount of buprenorphine that is suitable for topical application to the skin of a human or lower animal subject, in a single dose, according to good medical practice. As used herein, "topical" application refers to any method by which the compositions of this invention are placed in direct contact with the skin of a subject, or in indirect contact through a permeable interfacing material, such that the flux of buprenorphine from the patch through the skin is, for an adult (weighing approximately 70 kilograms), at least about 20 $\mu g$ (micrograms)/hr (hour), preferably from about 40 $\mu g$/hr to about 100 $\mu g$/hr.

The compositions of this invention are preferably administered by use of a device which contains the composition in close proximity to the skin, i.e., a "transdermal patch". Many such structures are known in the pharmaceutical literature. Such patches preferably apply a composition of this invention to an area of skin totalling from about 1 $cm^2$ to about 50 $cm^2$ (about 0.16 $in^2$ to about 7.75 $in^2$), more preferably from about 5 $cm^2$ to about 10 $cm^2$ (about 0.78 $in^2$ to about 1.55 $in^2$).

Buprenorphine

The compositions of this invention contain a safe and effective amount of buprenorphine. As used herein, "buprenorphine" refers to N-cyclopropylmethyl-7$\alpha$-[1-(S)-hydroxy-1,2,2-trimethylpropyl]6,14-endoethano-6,7,8,14-tetrahydronororipavine, and related compounds described in U.S. Pat. No. 3,433,791, Bentley, issued Mar. 18, 1969 (incorporated by reference herein). Pharmaceutically-acceptable salts of buprenorphine may also be used in compositions of this invention. Also, in addition to buprenorphine, the compositions of this invention may contain other active materials. Such additional active materials should not, however, substantially interfere with the transdermal delivery of buprenorphine or its desired therapeutic effects.

Polar solvent material

As used herein, "polar solvent material" refers to $C_3$-$C_4$ diols, $C_3$-$C_6$ triols, and mixtures thereof. Such polar solvent materials include, for example, 1,2-propane diol, 1,3-propane diol, 1,2-butane diol, 1,3-butane diol, 1,4-butane diol, 1,2,6-hexane triol, 1,2,5-pentane triol, 1,2,4-butane triol, 1,2,5-hexane triol, glycerol or mixtures thereof. Preferred polar solvent materials include 1,2-butane diol, 1,2-propane diol, glycerol, and 1,2,6-hexane triol. A particularly preferred polar solvent material is 1,2-propane diol (propylene glycol).

Polar lipid material

As used herein, "polar lipid material" refers to fatty alcohol esters, fatty acid esters, and mixtures thereof. These polar lipid materials include monoesters and diesters, containing from 6 to 18 carbon atoms in their longest carbon chain, having a melting point of less than about 50° C. (122° F.). Preferred monoesters have carbon chains of from 8 to 12 carbon atoms in length. Monoesters include saturated monoesters of a $C_6$-$C_{14}$ acid with a linear or branched $C_1$-$C_6$ alcohol, or of a $C_6$-$C_{14}$ alcohol with a linear or branched $C_2$-$C_6$ acid. Monoesters useful in this invention also include unsaturated monoesters of a $C_6$-$C_{18}$ acid with a linear or branched $C_1$-$C_6$ alcohol, and monoesters of a linear or branched $C_6$-$C_{18}$ alcohol with a $C_2$-$C_6$ acid. Diester polar lipid materials of this invention include diesters of a $C_2$-$C_8$ dicarboxylic acid with a linear or branched $C_1$-$C_6$ alcohol, and diesters of a $C_2$-$C_8$ linear or branched, dihydroxy alcohol with a $C_2$-$C_6$ acid.

Such polar lipid materials useful in the compositions of this invention include, for example, methyl caproate, propyl caproate, hexyl acetate, methyl heptylate, pentyl heptylate, heptyl acetate, heptyl caproate, methyl caprylate, propyl caprylate, octyl acetate, octyl butylate, methyl caprate, ethyl caprate, hexyl caprate, methyl pelargonate, butyl pelargonate, lauryl acetate, lauryl butylate, methyl laurate, ethyl laurate, isopropyl laurate, hexyl laurate, $C_{12}$-$C_{15}$ alcohols lactate, methyl myristate, ethyl myristate, isopropyl myristate, pentadecyl acetate, methyl palmitate, ethyl palmitate, isopropyl palmitate, hexadecyl acetate, methyl oleate, ethyl oleate, butyl oleate, dimethyl adipate, diisopropyl adipate, diisobutyl adipate, dimethyl maleate, diisopropyl malate, dibutyl malate, dihexyl maleate, and mixtures thereof. Preferred polar lipid materials include methyl caprylate, propyl caprylate, octyl acetate, methyl caproate, propyl caproate, methyl laurate, and $C_{12}$-$C_{15}$ alcohols lactate. Methyl caprylate, methyl laurate, and mixtures of methyl caproate and methyl caprylate are particularly preferred.

Optional components

The compositions of this invention may also contain pharmaceutically acceptable optional components that modify the physical and/or therapeutic effects of the compositions. Such optional components may include, for example, additional solvents, emulsifiers, gelling agents, fragrances, preservatives, and stabilizers. However, such optional materials must not unduly interfere with the transdermal delivery of buprenorphine. Optional components useful in the compositions of this invention are described in the following patent documents, incorporated by reference herein: European Patent Publication No. 43,738, Wickett et al., published Jan. 13, 1982; and U.S. Pat. No. 4,552,872, Cooper et al., issued Nov. 12, 1985.

A preferred optional material is a solvent or co-solvent material, which enhances the solubility of the polar lipid material and/or buprenorphine in the polar solvent material. Such solvent materials include, for example, short chain alcohols and ethers. Preferred optional solvent materials include ethanol, isopropanol, and dimethyl isosorbide. Such optional solvent materials are particularly preferred when the polar lipid material is a long chain ester poorly soluble in the polar solvent material (e.g., having carbon chains of from 14 to 18 carbon atoms in length).

Water may also be used as a solvent or co-solvent in the compositions of this invention. However, the presence of water may adversely affect the flux afforded by the compositions when the polar lipid material and/or the buprenorphine is near the level of saturation in the polar solvent material. If water is used in a saturated system, a gel or emulsion is preferably formed.

Thickeners, or gelling agents, are also preferred optional materials useful in the compositions of this invention. Thickeners among those useful herein include particulate thickeners and polymeric thickeners such as guargum, methylcellulose, methylhydroxypropylcellulose, polypropylcellulose, polypropylhydroxyethylcellulose, hydroxyethylcellulose, hydroxypropylcellulose and starches and starch derivatives.

The following non-limiting examples illustrate the compositions, processes and uses of the present invention.

EXAMPLE I

A transdermal patch was made, according to this invention, for delivery of buprenorphine. The buprenorphine composition comprised:

| Component | % (by weight) |
|---|---|
| buprenorphine | 0.83 |
| propylene glycol USP | 95.60 |
| methyl laurate | 2.77 |
| hydroxypropylcellulose NF | 0.80 |
| | 100.00 |

A baffled flask is configured to allow mixing of the components under a nitrogen blanket (to minimize water content of the composition). The propylene glycol is added to the flask, and while stirring, the hydroxypropylcellulose is added. The mixture is quickly heated, to approximately 100° C. (212° F.), dissolving the hydroxypropylcellulose. After dissolution, the mixture is slowly cooled to room temperature (approximately 27° C., 80° F.), to minimize vapors.

The methyl laurate is then added, and stirred for approximately 15 hours, at room temperature. The mixture is then heated, and the buprenorphine added slowly, followed by heating (to approximately 90° C., 194° F.) with stirring, to dissolve the buprenorphine. After dissolution, the composition is allowed to cool slowly. After cooling, the composition is transferred to a suitable storage container, under a nitrogen blanket.

A patch structure is made by placing a sheet of lens tissue measuring approximately 4 cm (centimeters)×10 cm, on a 5 cm×12 cm sheet of polymer coated metallized film. This film is, in turn, placed in the center of a 10 cm×17 cm sheet of nonwoven material, coated with an acrylic adhesive.

Approximately 600 mg (milligrams) of the gel composition made above is then placed on the lens tissue, and spread evenly. The patch is then applied to the skin of a human subject, experiencing post-operative pain, with the gel/tissue layer in direct contact with the skin. The subject's pain is reduced.

In the above example, other transdermal patch structures may be substituted for the patch structure described, with substantially similar results. Many structures useable herein are among those known in the art. Also, in the above example, methyl caproate, propyl caproate, hexyl acetate, methyl heptylate, pentyl heptylate, heptyl acetate, heptyl caproate, methyl caprylate, propyl caprylate, octyl acetate, octyl butylate, methyl caprate, ethyl caprate, hexyl caprate, methyl pelargonate, butyl pelargonate, lauryl acetate, lauryl butylate, ethyl laurate, isopropyl laurate, hexyl laurate, $C_{12}$–$C_{15}$ alcohols lactate, methyl myristate, ethyl myristate, isopropyl myristate, dimethyl adipate, diisopropyl adipate, diisobutyl adipate, dimethyl maleate, diisopropyl malate, dibutyl malate, dihexyl maleate, and mixtures thereof are substituted for methyl laurate, with substantially similar results.

EXAMPLE II

A buprenorphine composition, according to this invention, is made comprising:

| Component | % (by weight) |
|---|---|
| buprenorphine | 1.5 |
| propylene glycol | 89.2 |
| methyl caprylate | 8.5 |
| hydroxypropylcellulose | 0.8 |

The composition is made by mixing the compounds in a manner analogous to the method of Example I. Approximately 800 milligrams of this composition are placed in a suitable patch structure having a surface area of approximately 10 cm². When applied to the skin of a human subject, analgesia is produced.

EXAMPLE III

A buprenorphine composition, according to this invention, is made comprising:

| Component | % (by weight) |
|---|---|
| buprenorphine | 0.90 |
| propylene glycol | 84.20 |
| methyl caprylate | 2.5 |
| methyl cparoate | 2.5 |
| octanol | 4.95 |
| dimethyl isosorbide | 4.95 |

The methyl caprylate, methyl caproate, octanol and dimethyl isosorbide are added, separately, to a flask. The propylene glycol is then added, and the mixture mixed until a homogenous solution is obtained. The buprenorphine is then added, and the mixture is sonicated for approximately 15 minutes, heated to approximately 50° C. (122° F.) for approximately 30 minutes, and then stirred for approximately 50 hours at approximately 32° C. (90° F.). Approximately 0.5 ml of the composition is then placed in a patch structure, such as described in Example I. The patch, when applied to the skin of a human suffering pain, affords analgesia.

EXAMPLE IV

A buprenorphine ointment, according to this invention, is made comprising:

| Component | % (by weight) |
|---|---|
| buprenorphine | 1.0 |
| 1,2-butane diol | 79.5 |
| $C_{12}$–$C_{15}$ alcohols lactate | 9.0 |
| Brij 721* | 10.0 |
| fragrance | 0.5 |

*polyoxyethylene 21 stearyl ether, nonionic emulsifier, sold by ICI Americas, Inc.

The Brij 21 is melted, and mixed with a heated mixture of the 1,2-butane diol and $C_{12}$–$C_{15}$ alcohols lactate. The buprenorphine is added and stirred, and the mixture is cooled. This composition, when applied to the skin of a human subject suffering pain from metastatic cancer, affords analgesia.

What is claimed is:

1. A composition for the transdermal delivery of buprenorphine, comprising a safe and effective amount of buprenorphine in a carrier comprising:
   (a) a polar solvent material selected from the group consisting of $C_3$–$C_4$ diols, $C_3$–$C_6$ triols, and mixtures thereof; and
   (b) a polar lipid material selected from the group consisting of fatty alcohol esters, fatty acid esters, and mixtures thereof;
   wherein said polar solvent material and said polar lipid material are present in a weight ratio of solvent material:lipid material of from about 60:40 to about 99:1.

2. A composition for the transdermal delivery of buprenorphine, according to claim 1, wherein said polar solvent material and said polar lipid material are present at a combined level of from about 70% to about 99.5%.

3. A composition for the transdermal delivery of buprenorphine, according to claim 2, in unit dosage form containing from about 1.0 mg to about 40 mg of buprenorphine.

4. A composition for the transdermal delivery of buprenorphine, according to claim 1, wherein said polar lipid material is selected from the group consisting of monoesters of $C_6$–$C_{18}$ fatty acids, monoesters of $C_6$–$C_{18}$ fatty alcohols, diesters of $C_2$–$C_8$ dicarboxylic acids with $C_1$–$C_6$ alcohols, diesters of $C_2$–$C_8$ dihydroxy alcohols with $C_2$–$C_6$ acids, and mixtures thereof.

5. A composition for the transdermal delivery of buprenorphine, according to claim 4, wherein said polar solvent material is selected from the group consisting of 1,2-butane diol, 1,2-propane diol, glycerol and 1,2,6-hexane triol, and mixtures thereof.

6. A composition for the transdermal delivery of buprenorphine, according to claim 5, wherein said polar solvent material is 1,2-propane diol.

7. A composition for the transdermal delivery of buprenorphine, according to claim 6, wherein said polar lipid material is selected from the group consisting of methyl caprylate, propyl caprylate, octyl acetate, methyl caproate, propyl caproate, methyl laurate, $C_{12}$–$C_{15}$ alcohols lactate, and mixtures thereof.

8. A composition for the transdermal delivery of buprenorphine, according to claim 7, wherein said polar lipid material is methyl laurate.

9. A composition for the transdermal delivery of buprenorphine, according to claim 8, wherein the weight ratio of solvent material:lipid material is about 97:3.

10. A composition for the transdermal delivery of buprenorphine, according to claim 7, wherein said polar lipid material is methyl caprylate.

11. A composition for the transdermal delivery of buprenorphine, according to claim 10, wherein the weight ratio of solvent material:lipid material is from about 90:10 to about 95:5.

12. A composition for the transdermal delivery of buprenorphine, according to claim 2, additionally comprising a solvent material which enhances the solubility of said polar lipid material in said polar solvent material.

13. A composition for the transdermal delivery of buprenorphine, according to claim 2, additionally comprising a thickener.

14. A composition in unit dosage form, for the transdermal delivery of buprenorphine, comprising:
   (a) from about 3.0 mg to about 10 mg of buprenorphine; and
   (b) a carrier comprising
      (i) propylene glycol, and
      (ii) a polar lipid material selected from the group consisting of methyl caprylate, propyl caprylate, octyl acetate, methyl caproate, propyl caproate, methyl laurate, $C_{12}$–$C_{15}$ alcohols lactate, and mixtures thereof;
   wherein said polar solvent material and said polar lipid material are present at a combined level of from about 90% to about 99.5%; and wherein said polar solvent material and said polar lipid material are present in a weight ratio of solvent material:lipid material of from about 60:40 to about 99:1.

15. A composition in unit dosage form for the transdermal delivery of buprenorphine, according to claim 14, wherein said polar lipid material is methyl laurate.

16. A composition in unit dosage form for the transdermal delivery of buprenorphine, according to claim 14, wherein said polar lipid material is methyl caprylate.

17. A composition in unit dosage form for the transdermal delivery of buprenorphine, according to claim 14, additionally comprising a solvent material which enhances the solubility of said polar lipid material in said propylene glycol.

18. A composition in unit dosage form for the transdermal delivery of buprenorphine, according to claim 17, additionally comprising a thickener.

* * * * *